United States Patent
Reddy et al.

(10) Patent No.: US 7,700,779 B2
(45) Date of Patent: Apr. 20, 2010

(54) CRYSTALLINE FORMS OF FEXOFENADINE AND ITS HYDROCHLORIDE

(75) Inventors: M. Satyanarayana Reddy, Hyderabad (IN); S. Thirumalai Rajan, Hyderabad (IN); U. V. Bhaskara Rao, Hyderabad (IN)

(73) Assignees: Dr. Reddy's Laboratories Limited, Hyderabad (IN); Dr. Reddy's Laboratories, Inc., Bridgewater, NJ (US)

( * ) Notice: Subject to any disclaimer, the term of this patent is extended or adjusted under 35 U.S.C. 154(b) by 756 days.

(21) Appl. No.: 10/362,339

(22) PCT Filed: Jul. 31, 2001

(86) PCT No.: PCT/US01/23994

§ 371 (c)(1), (2), (4) Date: Nov. 12, 2003

(87) PCT Pub. No.: WO02/102777

PCT Pub. Date: Dec. 27, 2002

(65) Prior Publication Data

US 2004/0077683 A1   Apr. 22, 2004

(30) Foreign Application Priority Data

Jun. 18, 2001   (IN) .................... 484/MAS/2001

(51) Int. Cl.
*C07D 211/22* (2006.01)
(52) U.S. Cl. .................... 546/239; 546/240; 514/317
(58) Field of Classification Search ............ 546/239, 546/240; 514/317
See application file for complete search history.

(56) References Cited

U.S. PATENT DOCUMENTS

| 4,254,129 A | 3/1981 | Carr et al. ............ 424/267 |
| 5,675,009 A * | 10/1997 | King et al. ............ 546/239 |
| 6,153,754 A | 11/2000 | D'Ambra et al. |
| 2002/0177608 A1 | 11/2002 | Dolitzky et al. ....... 514/317 |
| 2002/0193603 A1 * | 12/2002 | Henton et al. ......... 546/238 |

FOREIGN PATENT DOCUMENTS

| WO | WO 95/31437 | * 11/1995 |
| WO | WO 95/31437 A1 | 11/1995 |
| WO | 97 23213 | 7/1997 |
| WO | 02 10115 | 2/2002 |
| WO | 02 080857 | 10/2002 |

OTHER PUBLICATIONS

Brittain "Polymorphism in pharmceutical solids" Marcel Dekker, p. 1-2 (1999).*

(Continued)

*Primary Examiner*—Celia Chang
(74) *Attorney, Agent, or Firm*—Robert A. Franks; Lee Banks; Anjum Swaroop

(57) ABSTRACT

The present invention is related to novel polymorph of Fexofenadine and Fexofenadine hydrochloride of formula 1 and process of preparation thereof. The present invention is also directed to provide pure novel polymorphs of Fexofenadine and its hydrochloride by a simple process which is cost effective, commercially viable and environment friendly.

24 Claims, 10 Drawing Sheets

OTHER PUBLICATIONS

Figure 1A:
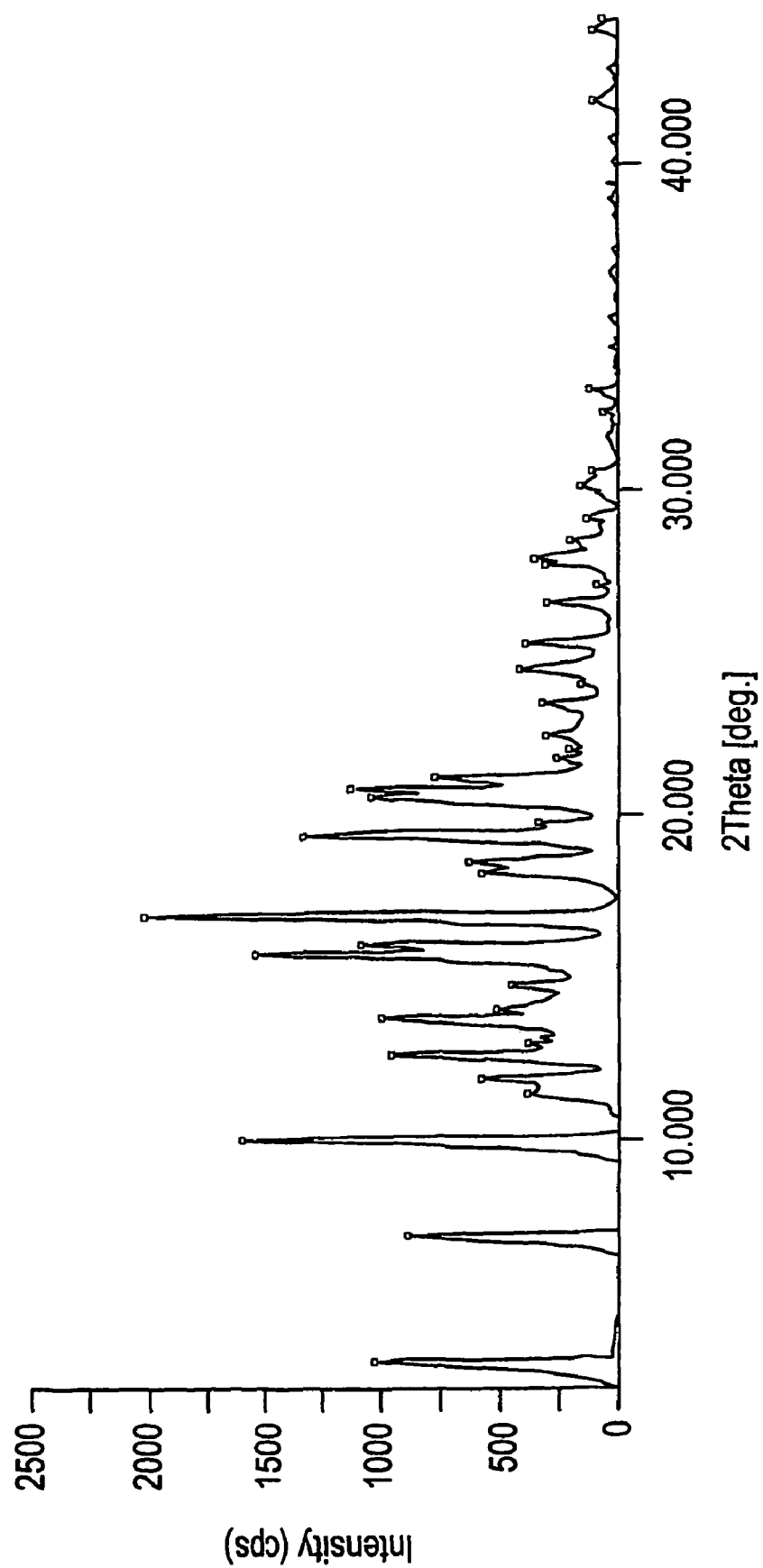

Brittain "Polymorphism in pharmaceutical solids" Maarcel Dekker, p. 1-2, 184-185 (1999).*
Internation Union of crystallogrphy, Google search result (2006).*
Index by Strukturbericht, gogle search result (2006).*
Davidovich et al. "Detection of . . . " Am. Pharm. Rev. v. 7(2) pp. 10, 12, 14, 15, 100 (2004).*
Wikipedia Internet encyclopedia (2006).*
Brittain "Polymorphism in pharmaceutical solids" p. 2, 185, 236 (1999).*
Berstein "Polymorphism in molecular crystals" p. 117-118, 272 (2002).*
Byrn et al. "Solid staate chemistry of drugs" p. 84-85 (1999).*
Exhibit A comparison of table 2 p. 8 and table 9 Henton.*
Kirk-Othmer "Encyclopedia of chemical technology" v.8, p. 95-147 (2002).*
US Pharmacopia #23, national formulary#18 (1995) p. 1843.*
Davidovich et al. "Detection of polymorphism . . . "Am. Pharm. Review 7(1)pp. 10, 12, 14, 15, 100 (2004).*
Berstain "Polymorphism in molecular crystals" p. 53 (2002).*
Fox et al. "Physics and chemistry . . . " p. 179-182 (1963).*
Byrn et al. "Solid state chemistry of drugs" p. 84-85 (1999).*
Exhibit A comparison of table 2 p. 8 and table 9 Henton (2007).*

* cited by examiner

FIG. 1B

Peak Search

| Peak No. | 2Theta | FWHM | d-value | Intensity | I/Io |
|---|---|---|---|---|---|
| 1 | 3.820 | 0.212 | 23.1110 | 1032 | 51 |
| 2 | 7.680 | 0.235 | 11.5018 | 886 | 44 |
| 3 | 10.660 | 0.235 | 8.2922 | 1614 | 79 |
| 4 | 12.060 | 0.400 | 7.3326 | 362 | 18 |
| 5 | 12.580 | 0.235 | 7.0306 | 579 | 28 |
| 6 | 13.260 | 0.212 | 6.6716 | 982 | 48 |
| 7 | 13.720 | 0.118 | 6.4489 | 331 | 16 |
| 8 | 14.360 | 0.188 | 6.1629 | 1016 | 50 |
| 9 | 14.680 | 0.235 | 6.0293 | 487 | 24 |
| 10 | 15.400 | 0.259 | 5.7490 | 465 | 23 |
| 11 | 16.300 | 0.212 | 5.4335 | 1525 | 75 |
| 12 | 16.620 | 0.188 | 5.3296 | 1064 | 52 |
| 13 | 17.480 | 0.235 | 5.0693 | 2036 | 100 |
| 14 | 18.880 | 0.212 | 4.6964 | 550 | 27 |
| 15 | 19.160 | 0.376 | 4.6284 | 649 | 32 |
| 16 | 19.960 | 0.235 | 4.4447 | 1334 | 66 |
| 17 | 20.360 | 0.235 | 4.3582 | 321 | 16 |
| 18 | 21.120 | 0.259 | 4.2031 | 1057 | 52 |
| 19 | 21.380 | 0.165 | 4.1526 | 1117 | 55 |
| 20 | 21.800 | 0.212 | 4.0735 | 770 | 38 |

FIG. 1C

Peak Search

| Peak No. | 2Theta | FWHM | d-value | Intensity | I/Io |
|---|---|---|---|---|---|
| 21 | 22.420 | 0.141 | 3.9622 | 242 | 12 |
| 22 | 22.640 | 0.118 | 3.9242 | 201 | 10 |
| 23 | 23.180 | 0.282 | 3.8340 | 281 | 14 |
| 24 | 24.020 | 0.259 | 3.7018 | 351 | 17 |
| 25 | 24.680 | 0.165 | 3.6043 | 151 | 7 |
| 26 | 25.060 | 0.188 | 3.5505 | 432 | 21 |
| 27 | 25.900 | 0.188 | 3.4372 | 402 | 20 |
| 28 | 27.160 | 0.165 | 3.2805 | 315 | 15 |
| 29 | 27.600 | 0.212 | 3.2292 | 84 | 4 |
| 30 | 28.320 | 0.118 | 3.1488 | 263 | 13 |
| 31 | 28.540 | 0.259 | 3.1250 | 353 | 17 |
| 32 | 29.040 | 0.235 | 3.0723 | 181 | 9 |
| 33 | 29.480 | 0.118 | 3.0274 | 83 | 4 |
| 34 | 29.720 | 0.259 | 3.0035 | 133 | 7 |
| 35 | 30.700 | 0.188 | 2.9099 | 162 | 8 |
| 36 | 31.160 | 0.141 | 2.8679 | 104 | 5 |
| 37 | 33.660 | 0.141 | 2.6604 | 105 | 5 |
| 38 | 42.600 | 0.141 | 2.1205 | 111 | 5 |
| 39 | 44.680 | 0.141 | 2.0265 | 109 | 5 |
| 40 | 44.820 | 0.118 | 2.0205 | 76 | 4 |

FIG. 4B

Peak Search

| Peak No. | 2Theta | FWHM | d-value | Intensity | I/Io |
|---|---|---|---|---|---|
| 1 | 5.000 | 0.118 | 17.6591 | 112 | 7 |
| 2 | 5.500 | 0.165 | 16.0548 | 1255 | 78 |
| 3 | 6.380 | 0.118 | 13.8422 | 128 | 8 |
| 4 | 6.800 | 0.165 | 12.9882 | 1051 | 65 |
| 5 | 10.660 | 0.165 | 8.2922 | 1001 | 62 |
| 6 | 10.960 | 0.165 | 8.0659 | 444 | 27 |
| 7 | 13.600 | 0.188 | 6.5055 | 307 | 19 |
| 8 | 14.140 | 0.165 | 6.2583 | 751 | 46 |
| 9 | 14.820 | 0.188 | 5.9726 | 464 | 29 |
| 10 | 15.060 | 0.141 | 5.8780 | 275 | 17 |
| 11 | 15.440 | 0.165 | 5.7342 | 215 | 13 |
| 12 | 15.980 | 0.212 | 5.5416 | 1616 | 100 |
| 13 | 16.360 | 0.165 | 5.4137 | 609 | 30 |
| 14 | 18.120 | 0.188 | 4.8916 | 1116 | 69 |
| 15 | 18.840 | 0.329 | 4.7063 | 1573 | 97 |
| 16 | 19.480 | 0.188 | 4.5531 | 1481 | 92 |
| 17 | 20.300 | 0.118 | 4.3710 | 369 | 23 |
| 18 | 20.540 | 0.259 | 4.3205 | 535 | 33 |
| 19 | 21.360 | 0.259 | 4.1564 | 363 | 22 |
| 20 | 22.000 | 0.212 | 4.0369 | 938 | 58 |
| 21 | 22.660 | 0.212 | 3.9208 | 92 | 6 |
| 22 | 23.380 | 0.235 | 3.8017 | 696 | 43 |
| 23 | 23.660 | 0.188 | 3.7573 | 256 | 16 |
| 24 | 24.180 | 0.212 | 3.6777 | 555 | 34 |
| 25 | 24.880 | 0.212 | 3.5758 | 535 | 33 |

FIG. 4C

Peak Search

| Peak No. | 2Theta | FWHM | d-value | Intensity | I/Io |
|---|---|---|---|---|---|
| 26 | 25.280 | 0.165 | 3.5201 | 159 | 10 |
| 27 | 26.000 | 0.376 | 3.4242 | 571 | 35 |
| 28 | 26.520 | 0.141 | 3.3582 | 80 | 5 |
| 29 | 26.780 | 0.118 | 3.3262 | 80 | 5 |
| 30 | 27.580 | 0.259 | 3.2315 | 166 | 10 |
| 31 | 28.120 | 0.235 | 3.1707 | 178 | 11 |
| 32 | 28.540 | 0.165 | 3.1250 | 186 | 11 |
| 33 | 29.320 | 0.188 | 3.0436 | 199 | 12 |
| 34 | 30.680 | 0.118 | 2.9117 | 79 | 5 |
| 35 | 30.840 | 0.118 | 2.8970 | 91 | 6 |
| 36 | 31.420 | 0.235 | 2.8448 | 182 | 11 |
| 37 | 31.800 | 0.165 | 2.8117 | 142 | 9 |
| 38 | 32.300 | 0.212 | 2.7693 | 95 | 6 |
| 39 | 32.980 | 0.259 | 2.7137 | 157 | 10 |
| 40 | 35.840 | 0.235 | 2.5034 | 98 | 6 |
| 41 | 37.080 | 0.165 | 2.4225 | 91 | 6 |
| 42 | 39.900 | 0.212 | 2.2576 | 95 | 6 |
| 43 | 41.060 | 0.259 | 2.1964 | 85 | 5 |
| 44 | 41.460 | 0.118 | 2.1762 | 78 | 5 |

CRYSTALLINE FORMS OF FEXOFENADINE AND ITS HYDROCHLORIDE

FIELD OF THE INVENTION

The present invention relates to a novel crystalline form of fexofenadine hydrochloride and to a process for the preparation thereof. More specifically, the present invention relates to a novel anhydrous crystalline Form X of fexofenadine hydrochloride. The present invention also relates to a novel crystalline form of fexofenadine, particularly Form A of fexofenadine and to a process for the preparation thereof.

BACKGROUND OF INVENTION

Chemically fexofenadine hydrochloride is 4-[4-[4-(hydroxydiphenylmethyl)-1-piperidinyl]-1-hydroxybutyl]-α,α-dimethylbenzene acetic acid hydrochloride. It is also known as terfenadine carboxylic acid metabolite. It is represented by Formula 1.

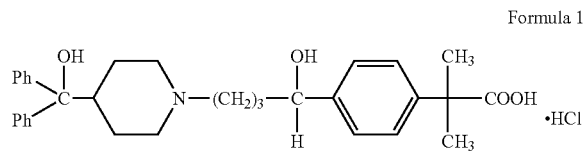

Formula 1

Fexofenadine hydrochloride is useful as an antihistamine, and does not cause the adverse effects associated with the administration of terfenadine including abnormal heart rhythms in some patients with liver disease or patients who also take the antifungal drug ketoconazole or the antibiotic erythromycin.

U.S. Pat. No. 4,254,129 ("the '129 patent") entitled Piperidine Derivatives issued on Mar. 3, 1981. The '129 patent relates to substituted piperidine derivatives and methods of making and using them. The disclosed compounds, including fexofenadine and its pharmaceutically acceptable salts and individual optical isomers, are purported to be useful as antihistamines, antiallergy agents and bronchodilators.

The '129 patent discloses a process for the preparation of fexofenadine having a melting point of 195-197° C. The recrystallization process exemplified therein in Example 3, column 13, involves use of a mixture of solvents for preparation of fexofenadine.

WO 95/31437 discloses processes for preparing hydrated and anhydrous forms of piperidine derivatives, polymorphs and pseudomorphs thereof, which are useful as antihistamines, antiallergic agents and bronchodilators.

WO 95/31437 discloses the preparation of anhydrous forms of fexofenadine hydrochloride by subjecting the hydrated fexofenadine hydrochloride to an azeotropic distillation or to water minimizing recrystallization. In the invention described in this application, unlike the process described in WO 95/31437, hydrated Fexofenadine Hydrochloride is not converted to anhydrous Fexofenadine Hydrochloride, but instead Fexofenadine is converted to Form A of Fexofenadine and then to anhydrous Form X of Fexofenadine Hydrochloride. The novel anhydrous crystalline form of Fexofenadine Hydrochloride is obtained according to the present invention directly from the novel precursor i.e. Fexofenadine without generating a hydrated form. The starting material used Fexofenadine (Base) is different than described in WO 95/31437.

WO 00/71124A1 discloses amorphous fexofenadine hydrochloride process, its preparation and a composition containing it.

Fexofenadine obtained in the prior art processes, is a mixture of regioisomers of fexofenadine containing 33% of para isomer and 67% of meta isomer. These components are referred to as inseparable and it is also stated that it is not possible to obtain either of the regioisomers in substantially pure form. On the other hand, Fexofenadine prepared according to the process of this invention has a purity of >99.5%. In the novel crystalline Fexofenadine of this invention, the meta isomer of Fexofenadine is at a level of below 0.1%. Purity of fexofenadine is critical when it is used for the conversion to its hydrochloride salt since it is very difficult to remove any undesired impurities, including regioisomers, from the desired compound in last late processing stage. Removing the impurities increases the cost of production. Hence it is generally preferred that the HPLC purity of fexofenadine is greater than 99.5%.

Another beneficial aspect of the present invention is that, the fexofenadine hydrochloride is obtained in almost quantitative yield from the precursor i.e. fexofenadine. Almost quantitative yield means that the pure fexofenadine is converted to fexofenadine hydrochloride quantitatively (>92% yield of theory), with almost no yield loss, as the fexofenadine base itself is >99.5% pure as compared to fexofenadine prepared by the prior art processes.

SUMMARY OF THE INVENTION

Therefore, an object of the present invention is to provide a novel crystalline form of fexofenadine and a process for its preparation.

Another object of the present invention is to provide a novel anhydrous crystalline form of fexofenadine hydrochloride (Formula 1) and a process for its preparation, which can be obtained directly from fexofenadine without generating a hydrated form of fexofenadine hydrochloride.

A further object of the present invention is to provide pure novel polymorphs of fexofenadine and its hydrochloride by a simple process which is cost effective, commercially viable and environmentally friendly.

BRIEF DESCRIPTION OF ACCOMPANYING DRAWINGS

FIG. 1 is a characteristic X-ray powder diffraction pattern of Form A of fexofenadine. Vertical axis: Intensity (CPS); Horizontal axis: Two Theta (degrees). The significant d values (A°) obtained are 23.11, 11.50, 8.29, 7.03, 6.67, 6.16, 6.02, 5.75, 5.43, 5.33, 5.07, 4.69, 4.63, 4.44, 4.20, 4.15, 4.07, 3.55, and 3.44.

Figure 2:
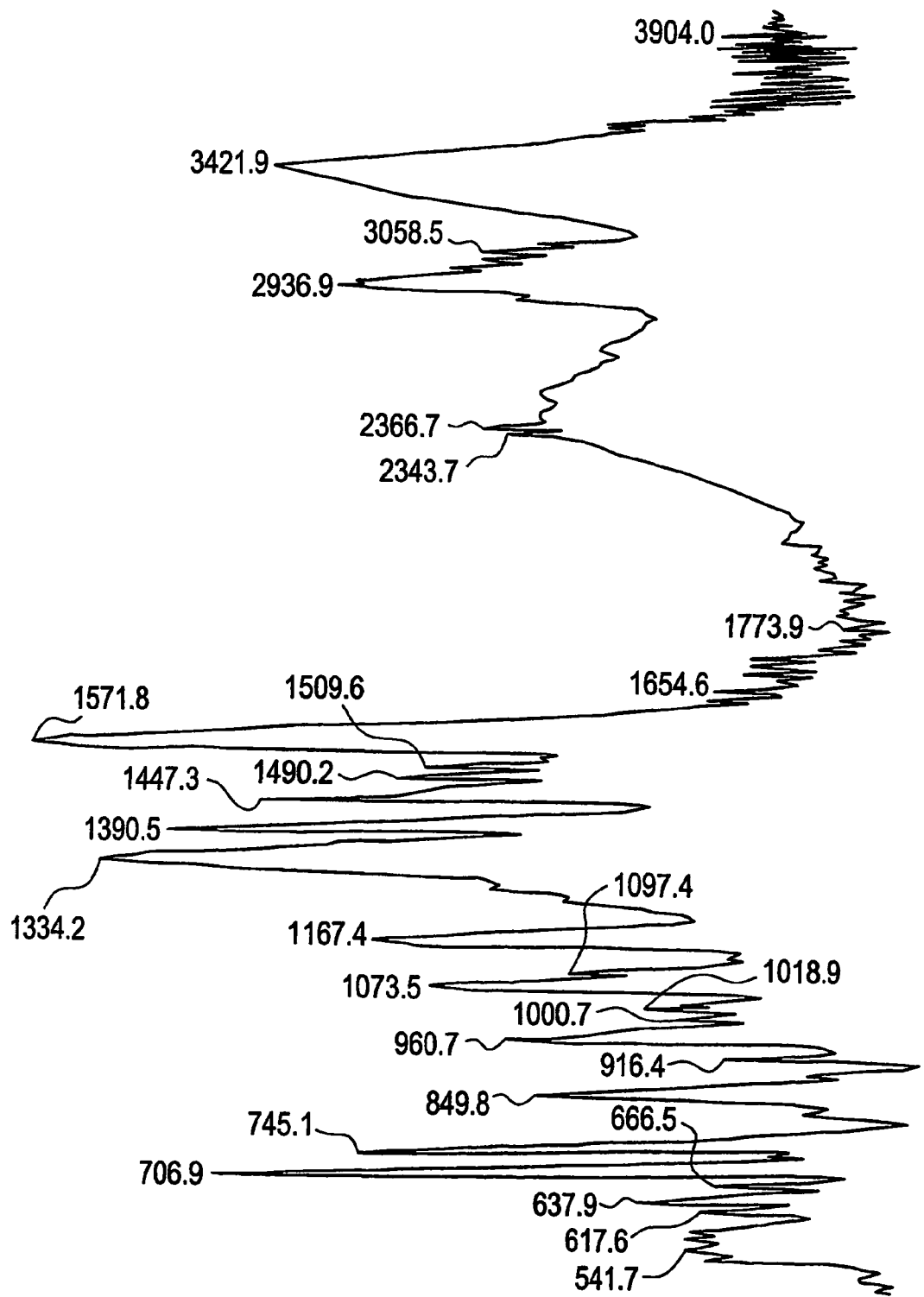

FIG. 2 is a characteristic infrared absorption spectrum in potassium bromide of aforementioned Form A of fexofenadine. [Vertical axis, Tramission (%); Horizontal axis: Wave number ($cm^{-1}$)]. The characteristic peaks for Form A are indicated at 3421, 3058, 2936, 2366, 2343, 1571, 1509, 1490, 1447, 1390, 1334, 1167, 1097, 1073, 1018, 960, 916, 849, 745, 706, 666, 637, 617, 541.

Figure 3:
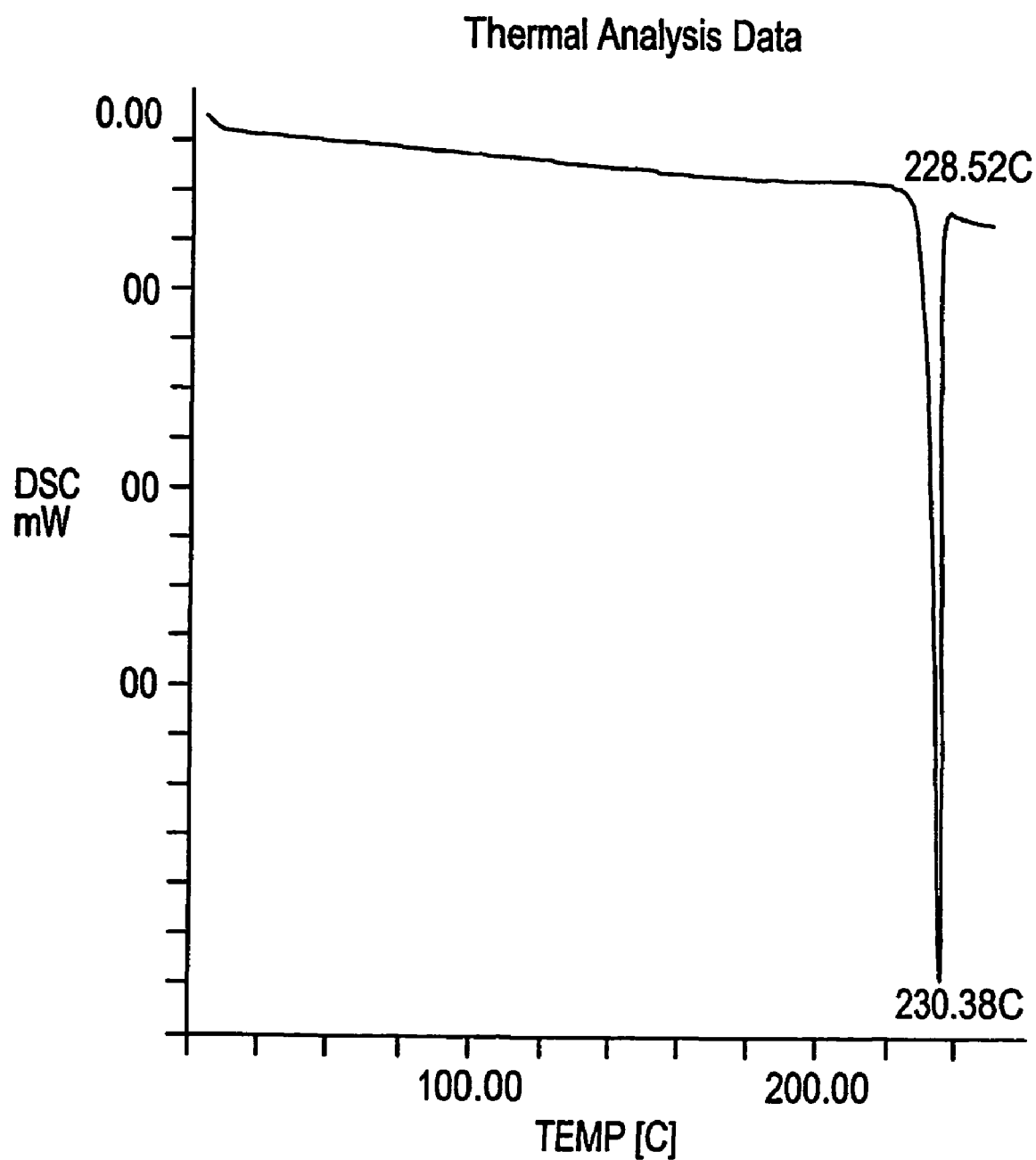

FIG. 3 is a characteristic of differential scanning calorimetry thermogram of aforesaid Form A of Fexofenadine. Vertical axis: mW; Horizontal axis: Temperature (° C.). The DSC thermogram exhibits a melt endotherm at about 230.38° C.

Figure 4A:
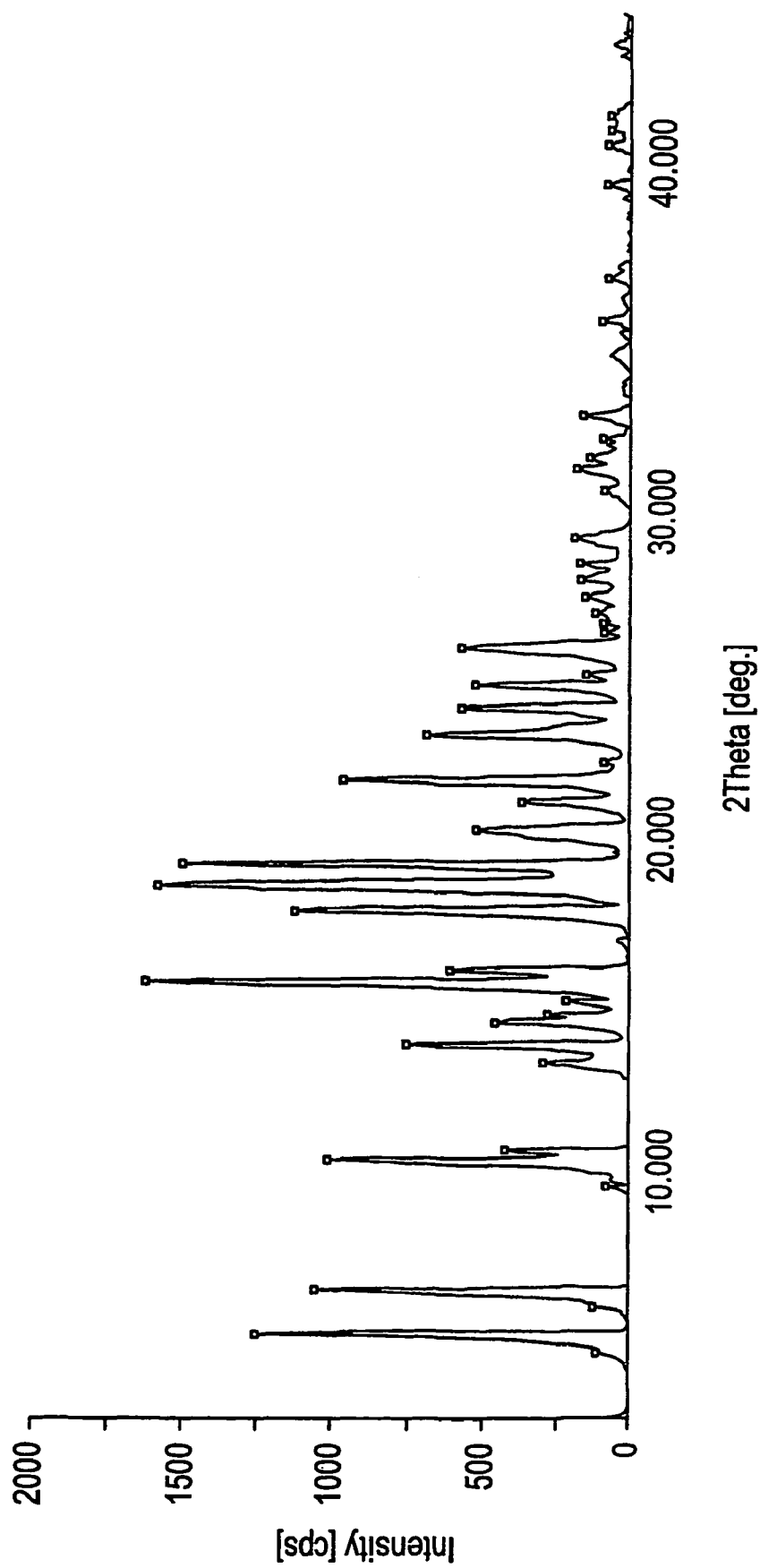

FIG. 4 is a characteristic X-ray powder diffraction pattern of Form X of fexofenadine hydrochloride. Vertical axis: Intensity (CPS); Horizontal axis: Two Theta (degrees). The significant d values (A°) obtained are 16.05, 12.98, 8.29, 8.06, 6.25, 5.97, 5.54, 5.41, 4.89, 4.70, 4.55, 4.37, 4.32, 4.15, 4.03, 3.80, 3.67, 3.57, 3.42.

Figure 5:
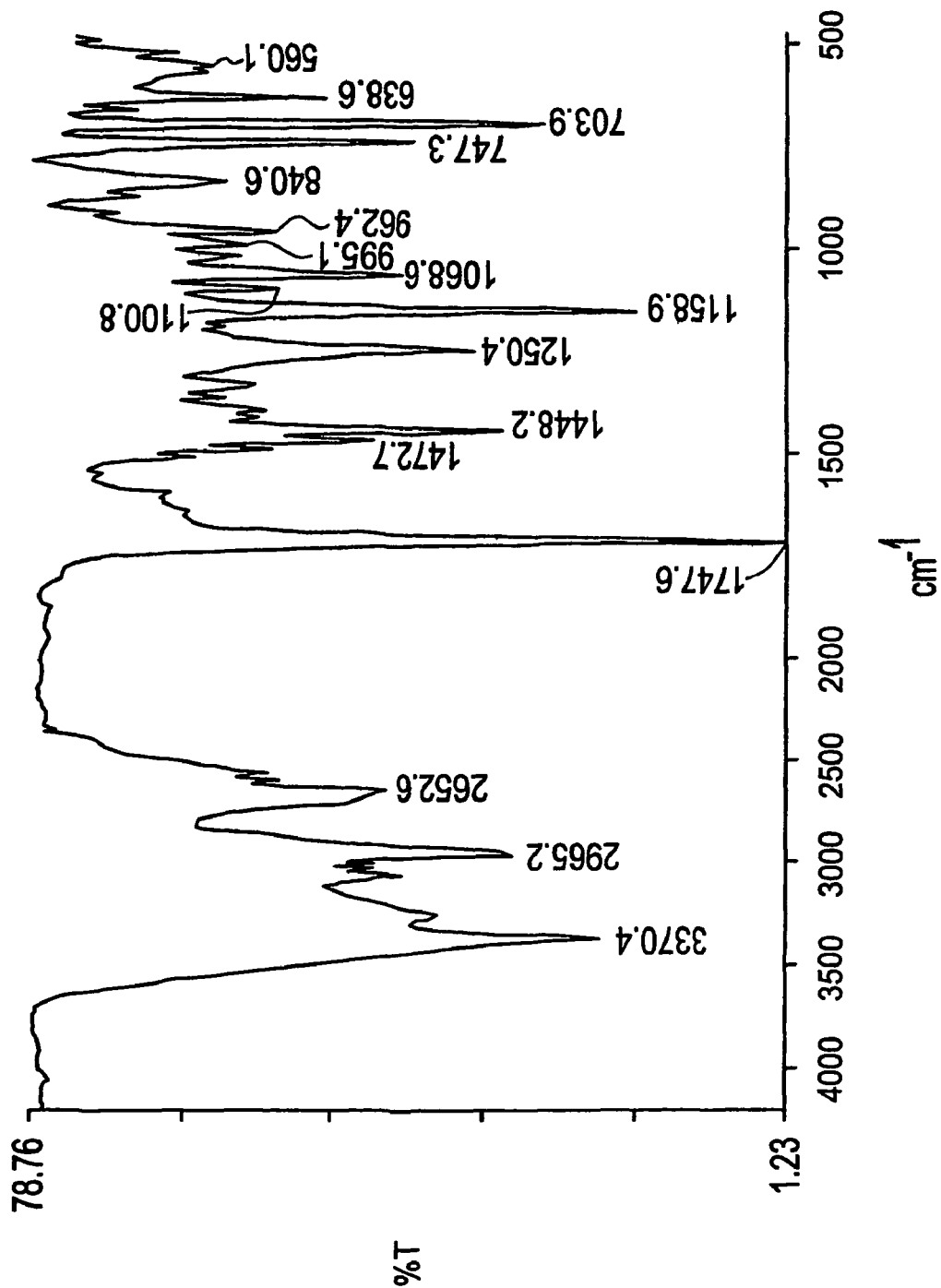

FIG. 5 is a characteristic infrared absorption spectrum in potassium bromide of aforementioned Form X of Fexofenadine hydrochloride. [Vertical axis, Tramission (%); Horizontal axis: Wave number ($cm^{-1}$)]. The characteristic peaks for Form X are indicated at 3370, 2965, 2652, 1717, 1472, 1448, 1250, 1158, 1100, 1068, 995, 962, 840, 747, 703, 638, 560.

Figure 6:
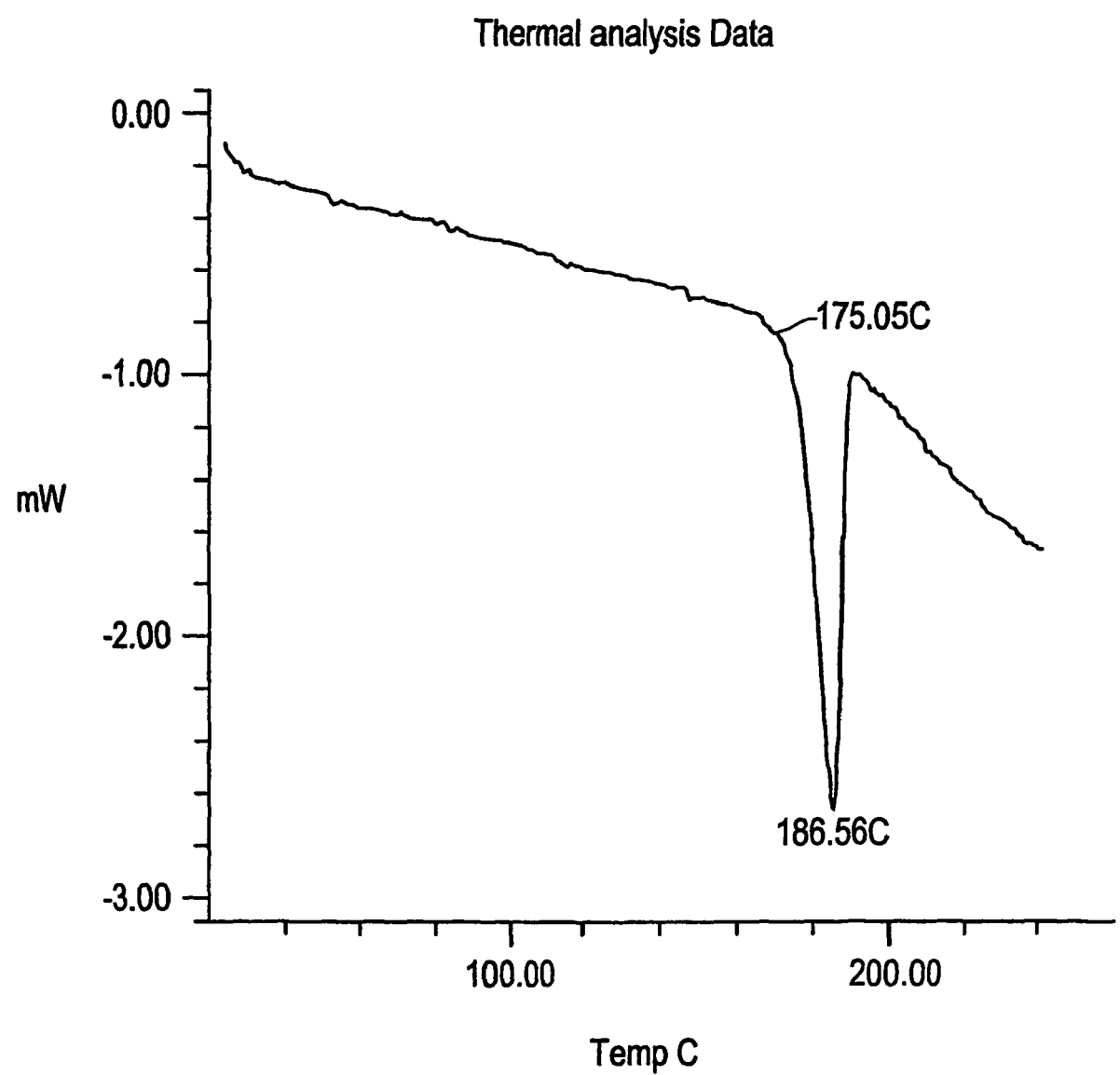

FIG. 6 is a characteristic of differential scanning calorimetry thermogram of aforesaid Form X of Fexofenadine hydrochloride. Vertical axis: mW; Horizontal axis: Temperature (° C.). The DSC thermogram exhibits a melt endotherm at about 186.56° C.

DETAILED DESCRIPTION OF INVENTION

The present invention provides a novel crystalline form of Fexofenadine, which is designated as Form A for convenience. The process for the preparation of novel crystalline Form A, comprises recrystallization of crude fexofenadine in an alcohol followed by azeotropically refluxing Fexofenadine in a non polar organic solvent, organic solvent or a mixture thereof and the subsequent isolation of the desired Form A.

Form A is prepared by a process, which comprises:

a. recrystallizing crude Fexofenadine in a ($C_1$-$C_3$) alkanol followed by;

b. azeotropically refluxing Fexofenadine in a non polar organic solvent, an organic solvent or a mixture thereof for 15 minutes to 6 hours, preferably 1-3 hours;

c. stirring the reaction mixture at ambient temperature for 30 minutes to 2 hours; and d. isolating the Form A of Fexofenadine by conventional methods.

Crude fexofenadine can be recrystallized in methanol, ethanol or isopropanol, preferably methanol. The ratio of crude Fexofenadine to the ($C_1$-$C_3$) alkanol is 1:10-20. The ratio of fexofenadine to nonpolar organic solvent and/or organic solvent in step b) is 1:10-15.

The non polar organic solvents referred to herein are selected from xylene or toluene or a ($C_6$-$C_9$) alkyl such as n-hexane, hexane, heptane, octane, nonane or cyclohexane. Toluene is the preferred non polar organic solvent. The organic solvents are ($C_1$ to $C_4$) alkyl acetates and are selected from methyl, ethyl, propyl, and butyl acetate, preferably ethyl acetate.

The Form A of Fexofenadine can be identified by the following characteristics:

a visual melting point (capillary tube) in the range of about 218-228° C.;

a melting endotherm at about 227-231° C. as determined by differential scanning calorimetry;

and an X-ray powder diffraction pattern essentially as shown in the Table 1.

TABLE 1

| D-Space, Angstroms | Intensity, $I/I_o$, % |
|---|---|
| d value | I/Io |
| 23.11 | 51 |
| 11.50 | 44 |
| 8.29 | 79 |
| 7.03 | 28 |
| 6.67 | 48 |
| 6.16 | 50 |
| 6.02 | 24 |
| 5.75 | 23 |
| 5.43 | 75 |
| 5.33 | 52 |
| 5.07 | 100 |
| 4.69 | 27 |
| 4.63 | 32 |
| 4.44 | 66 |
| 4.20 | 52 |
| 4.15 | 55 |
| 4.07 | 38 |
| 3.55 | 21 |
| 3.44 | 20 |

According to another aspect, the present invention provides a process for preparing a novel crystalline form of Fexofenadine Hydrochloride, designated as Form X.

The process for the preparation of novel crystalline Form X of fexofenadine hydrochloride, comprises reaction of fexofenadine Form A in non polar solvent, with a suitable solvent containing hydrogen chloride and isolating the desired Form X of fexofenadine hydrochloride which can be obtained directly from fexofenadine without generating a hydrated form of fexofenadine hydrochloride.

The Form X polymorph is prepared by a process, which comprises:

a. recrystallizing crude Fexofenadine in ($C_1$-$C_3$) alkanol followed by, b. azeotropically refluxing Fexofenadine in a non polar organic solvent, an organic solvent or mixtures thereof for 15 minutes to 6 hours, preferably 1-3 hours;

c. stirring the reaction mixture at ambient temperature for 30 min to 2 hours;

d. optionally isolating the Fexofenadine Form A by conventional methods;

e. if isolated, suspending Fexofenadine Form A, in a non polar organic solvent;

f. adjusting the pH of the reaction mass to 1 to 3, preferably 2 with a suitable solvent containing hydrogen chloride;

g. stirring the reaction mass for 30 minutes to 18 hours, preferably 1-10 hours and more preferably 3-6 hours at ambient temperature;

h. filtering the solid obtained followed by drying at 60-100° C.;

i. suspending the solid obtained in step (h) in an alkyl acetate and heating the reaction mixture to reflux for 0.5-6 hours preferably 1-3 hours;

j. stirring the reaction mixture at ambient temperature for 20 minutes to 2 hours; and k. isolating the anhydrous crystalline Form X of 4-[4-[4-(hydroxydiphenylmethyl)-1-piperidinyl]-1-hydroxybutyl]-α,α-dimethylbenzene acetic acid hydrochloride, by conventional methods.

The preparation of Form X can be accomplished without isolation of Form A. The preparation of Form X can proceed directly from step (c) to step (f) eliminating steps (d) and (e).

In variation of above process the preparation of novel Form X polymorph may be accomplished by drying the solid obtained in step (h) at 110-160° C. under reduced pressure for 30 minutes to 10 hours, preferably 2-5 hours.

The ratio of solid to alkyl acetate in step (i) is 1:10-15.

Yet another aspect of the present invention is to provide a process for preparing a novel crystalline form of Fexofenadine Hydrochloride, designated as Form X, by seeding technique.

This process comprises:

a. recrystallizing crude Fexofenadine in a ($C_1$-$C_3$) alkanol followed by;

b. azeotropically refluxing Fexofenadine in a non polar organic solvent for 3-4 hours;

c. optionally isolating the Fexofenadine Form A obtained in step b) by conventional methods accompanied by drying at below 100° C.;

d. suspending the Fexofenadine Form A obtained in step c) or adding to the mixture of step b) a mixture of a nonpolar organic solvents selected from toluene or xylene or a ($C_6$-$C_9$) alkyl; or an organic solvent selected from ($C_1$-$C_4$) alkyl acetate preferably ethyl acetate; and isopropanol, the ratio of solvent to isopropanol being 7-9:3-1 preferably 9:1;

e. adjusting the pH of the solution of step d) to 1 to 3 preferably 2 with a suitable solvent containing hydrogen chloride;

f. filtering the solution obtained in step e) to remove particulate matter;

g. seeding the solution of step f) with crystals of novel crystalline Form X and stirring the reaction mass at ambient temperature to separate the solid;

h. filtering the solid obtained in step g) followed by washing with a nonpolar organic solvent, organic solvent or hydrocarbon solvent; and i. drying the anhydrous crystalline Form X of 4-[4-[4-(hydroxydiphenylmethyl)-1-piperidinyl]-1-hydroxybutyl]α,α-dimethylbenzene acetic acid hydrochloride at 70-100° C.

The crude fexofenadine may be recrystallized in a $C_1$-$C_3$ alkanol such as methanol, ethanol or isopropanol, preferably, methanol.

The non polar organic solvents referred to herein are selected from xylene or toluene or a ($C_6$-$C_9$) alkyl such as n-hexane, hexane, heptane, octane, nonane or cyclohexane. Mixtures of solvents maybe used thereof Toluene is the preferred solvent. The organic solvents are ($C_1$-$C_4$) alkyl acetates and are selected from methyl, ethyl, propyl and butyl acetate preferably ethyl acetate.

The suitable solvent containing hydrogen chloride referred to herein is selected from methanol, ethanol, isopropanol or t-butanol, preferably isopropanol.

The ratio of crude fexofenadine to the $C_1$-$C_3$ alkanol is 1:10-20. The ratio of fexofenadine to the solvents in step b. is 1:10-15.

The hydrocarbon solvent is selected from hexane or cyclohexane, preferably cyclohexane.

The Form X of Fexofenadine hydrochloride obtained by the processes described above can be identified by a visual melting point (capillary tube) in the range of about 180-188° C.;

a melting endotherm at about 180-189° C. as determined by differential scanning calorimetry;

and an X-ray powder diffraction pattern essentially as shown in the Table 2.

TABLE 2

| D-Space, Angstroms | Intensity, $I/I_o$, % |
|---|---|
| d value | I/Io |
| 16.05 | 78 |

TABLE 2-continued

| D-Space, Angstroms | Intensity, $I/I_o$, % |
|---|---|
| 12.98 | 65 |
| 8.29 | 62 |
| 8.06 | 27 |
| 6.25 | 46 |
| 5.97 | 29 |
| 5.54 | 100 |
| 5.41 | 38 |
| 4.89 | 69 |
| 4.70 | 97 |
| 4.55 | 92 |
| 4.37 | 23 |
| 4.32 | 33 |
| 4.15 | 22 |
| 4.03 | 58 |
| 3.80 | 43 |
| 3.67 | 34 |
| 3.57 | 33 |
| 3.42 | 35 |

The present invention provides a improved method for the preparation of Fexofenadine Form A in its pure form by a crystallization process which requires only a single solvent. This solvent may be recovered and reused, thereby rendering the process cost effective and environmentally friendly.

The novel polymorphic forms of fexofenadine of this invention may if desired be converted into one of its pharmaceutically acceptable salts.

It is noteworthy to mention that both Fexofenadine and its hydrochloride obtained by the present invention are pure and well suited for formulation. Most pharmaceuticals formulation processes are faciliated by use of the active materials that are free flowing high melting solids. The novel anhydrous crystalline Form A and X of Fexofenadine Hydrochloride of the present invention are a high melting solid, very suited for formulation.

EXAMPLES

The present invention is illustrated by the following examples, which are not intended to limit the effective scope of the claims.

Reference Example

For the Preparation of Fexofenadine Crude

To a solution of a mixture of methyl 4-[4-[4-(hydroxydiphenylmethyl)1-piperidinyl]-1-oxobutyl]-α,α-dimethylbenzeneacetate hydrochloride and methyl 3-[4-[4-(hydroxydiphenylmethyl)1-piperidinyl]-1-oxobutyl]-α,α-dimethylbenzeneacetate hydrochloride (100 g) in methanol (600 ml) is added aqueous sodium hydroxide (36.4 g sodium hydroxide in 132 ml of water). The mixture is heated to reflux for about 2-4 hours. Completion of the reaction is monitored by TLC method and upon completion the reaction mixture is cooled to ambient temperature accompanied by addition of sodium borohydride (6.8 g). The reaction mixture is heated to 50-60° C. and maintained at the same temperature for about 14 hours (completion of the reaction is monitored by TLC method), and subsequently cooled to ambient temperature accompanied by carbon treatment. The clear filtrate obtained after carbon treatment, is stripped of methanol followed by addition of water (300 ml) and acetone (200 ml). The pH of the reaction mixture is then adjusted to ~6 with acetic acid, stirred for 5 hours and then filtered, followed by water wash (200 ml) to afford crude Fexofenadine.

Yield: 72 g

Example 1

Preparation of Pure Fexofenadine

A solution of Fexofenadine crude (500 g; prepared as per reference example) in methanol (4000 ml) is refluxed for 1 hour and the reaction mixture is then cooled to room temperature. The precipitated pure Fexofenadine obtained was filtered and washed with methanol (250 ml). Repeated recrystallization in methanol afforded pure Fexofenadine of desired purity.

Purity by HPLC 99.85%; Meta isomer<0.1%

Example 2

Step 1

Preparation of Form A from Pure Fexofenadine

A suspension of pure Fexofenadine (180 g) in toluene (1800 ml) is azeotropically refluxed for 2 and a half hours. The reaction mixture is then cooled to room temperature and stirred for about 40 minutes. After completion of this step the reaction mixture was filtered and washed with toluene (180 ml) and the obtained Form A of Fexofenadine is dried at 80-85° C. under atmospheric pressure till constant weight.

Yield 179.2 g: M.R (melting range) 220-224° C.

Step 2

Preparation of Form X of Fexofenadine Hydrochloride

To the Fexofenadine Form A (170 g; prepared as per procedure in step 1), toluene (1700 ml) is added followed by slow addition of isopropanol hydrogen chloride (prepared by purging hydrogen chloride to isopropyl alcohol) to pH 2. The reaction mass is then stirred for 10 hours 15 minutes. The solid obtained is filtered, washed with toluene (170 ml) and dried under vacuum at 75-80° C. Solid thus obtained (140 g) is refluxed in ethyl acetate (2800 ml) for about 1 hour. The reaction mixture is then cooled to room temperature and stirred for 1 hour 30 minutes. The reaction mass is filtered and washed with ethyl acetate (140 ml). The desired Form X of Fexofenadine hydrochloride is obtained after drying at 78-85° C. under atmospheric pressure till constant weight.

Yield 129.6 g: M.R 183-187° C.

Example 3

Preparation of Form X of Fexofenadine Hydrochloride

To the Fexofenadine Form A (95 g; prepared as per procedure under Example 2, step 1), toluene (950 ml) is added followed by slow addition of isopropanol hydrogen chloride (prepared by purging hydrogen chloride to isopropyl alcohol) to pH 2. The reaction mass is then stirred for 2 hours 45 minutes. The reaction mass is filtered and washed with toluene (95 ml) to isolate solid which is dried at 80-85° C. under atmospheric pressure till constant weight.

Part of the above-obtained solid was kept in oven to remove residual organic solvents at 141-149° C. at 100-mbar pressure, for 3 and half hours, to afford desired Form X of Fexofenadine Hydrochloride M.R 183-188° C.

Example 4

Preparation of Form X of Fexofenadine Hydrochloride

To pure Fexofenadine (50 g), toluene (500 ml) is added and the mixture is refluxed azeotropically for about 3 hours. The reaction mass is then cooled to room temperature followed by slow addition of isopropanol hydrogen chloride, to pH 2. The reaction mass is then stirred for about 15 and a half hours. The separated solid is filtered, washed with toluene (50 ml) and dried (Yield 43.3 g). Part of this solid (42 g) is suspended in ethyl acetate (420 ml) and refluxed for about 1 hour (this operation was performed for removal of residual organic solvents). The suspension is then cooled to room temperature and stirred for 20 minutes. The reaction mass is filtered and washed with ethyl acetate (42 ml). The desired Form X of Fexofenadine hydrochloride is dried at 90-96° C. to constant weight.

Yield 39 g: M.R 183-188° C.

Example 5

A suspension of pure Fexofenadine (prepared as per example 1; 100 g) in toluene (1000 ml) is azeotropically refluxed for 3-4 hours. The reaction mixture is then cooled to room temperature and stirred for about 15-30 minutes. Subsequently, the reaction mixture is filtered and washed with toluene (100 ml) and the Fexofenadine Form A obtained is dried below 100° C. to constant weight.

Yield 95 g

To a mixture of ethyl acetate and isopropanol (900:100 ml), is added Fexofenadine Form A (100 g; prepared as per above procedure), followed by slow addition of isopropanol hydrogen chloride (prepared by purging hydrogen chloride to isopropyl alcohol) to pH 2. The reaction mass is then filtered and to the filtrate is added several crystals of Form X of 4-[4-[4-(hydroxydiphenylmethyl)-1-piperidinyl]-1-hydroxybutyl]-α,α-dimethylbenzene acetic acid hydrochloride. The reaction mixture is then stirred for 2-4 hours. The solid obtained is filtered, washed with cyclohexane (200 ml) and dried below 100° C. to constant weight to obtain the desired Form X of Fexofenadine Hydrochloride Yield 100 g.

The aforementioned crystalline form X of Fexofenadine hydrochloride and Form A of Fexofenadine, in Examples 2-4 have been examined for their structural and analytical data viz., Powder X-Ray Diffraction, Differential Scanning Calorimetry, and Infrared Absorption Spectroscopy.

The results obtained are discussed above and the respective drawings attached (FIGS. 1-6).

The X-Ray Diffraction Pattern set out herein were obtained using Rigaku D/Max-2200 X-Ray Powder Diffractometer having a Cu K-radiation source of wavelength λ=1.54 A°. The samples were scanned between 3-45 degrees 2θ.

The infrared absorption spectra were recorded in solid state as KBr dispersion on Perkin Ehner 1650 FT-IR spectrophotometer.

Differential Scanning Calorimetric analysis was performed on a Shimadzu DSC-50. The samples were heated to 250° C. at a heating rate of 5° C./min with a 30 ml/minute nitrogen purge.

The invention claimed is:
1. A crystalline Fexofenadine Hydrochloride which is characterized by the following X-ray powder diffraction pattern (d values in Å): 16.05, 12.98, 8.29, 8.06, 6.25, 5.97, 5.54, 5.41, 4.89, 4.70, 4.55, 4.37, 4.32, 4.15, 4.03, 3.80, 3.67, 3.57, 3.42.
2. A process for preparing crystalline Fexofenadine Hydrochloride according to claim 1 which comprises:
   a. recrystallizing crude Fexofenadine in a ($C_1$-$C_3$) alkanol;
   b. azeotropically refluxing the recrystallized Fexofenadine in a non polar organic solvent or organic solvent or a mixture thereof for 15 minutes to 6 hours;
   c. stirring the reaction mixture at ambient temperature for 30 mm to 2 hours;
   d. adjusting the pH, of the reaction mass to 1 to 3 with a solvent containing hydrogen chloride;
   e. stirring the reaction mass for 30 minutes to 18 hours at ambient temperature;
   f. filtering the solid obtained followed by drying at 60-100° C.;
   g. suspending the solid obtained in step (f) in an alkyl acetate and heating the reaction mixture to reflux for 30 minutes to 6 hours;
   h. stirring the reaction mixture at ambient temperature for 20 minutes to 2 hours; and
   i. isolating the anhydrous crystalline fexofenadine hydrochloride.
3. A process for preparing crystalline Fexofenadine Hydrochloride according to claim 1 which comprises:
   a. recrystallizing crude Fexofenadine in a ($C_1$-$C_3$) alkanol;
   b. azeotropically refluxing the recrystallized Fexofenadine in a non polar organic solvent, organic solvent or a mixture thereof for 15 minutes to 6 hours;
   c. stirring the reaction mixture at ambient temperature for 30 mm to 2 hours;
   d. isolating crystalline Fexofenadine characterized by the following X-ray powder diffraction pattern (d values in Å): 23.11, 11.50, 8.29, 7.03, 6.67, 6.16, 6.02, 5.75, 5.43, 5.33, 5.07, 4.69, 4.63, 4.44, 4.20, 4.15, 4.07, 3.55, and 3.44;
   e. suspending the isolated crystalline Fexofenadine from step (d) in a non polar organic solvent;
   f. adjusting the pH, of the reaction mass to 1 to 3 with a solvent containing hydrogen chloride;
   g. stirring the reaction mass for 30 minutes to 18 hours at ambient temperature;
   h. filtering the solid obtained followed by drying at 60-100° C. or by drying at 110-16 under reduced pressure;
   i. suspending the solid obtained in step (h) in an alkyl acetate and heating the reaction mixture to reflux for 30 minutes-6 hours;
   j. stirring the reaction mixture at ambient temperature for 20 minutes to 2 hours; and
   k. isolating the anhydrous crystalline fexofenadine hydrochloride.
4. A process for preparing crystalline Fexofenadine Hydrochloride according to claim 1, which comprises:
   a) recrystallizing crude Fexofenadine in a ($C_1$-$C_3$) alkanol;
   b) azeotropically refluxing the recrystallized Fexofenadine in a non polar organic solvent for 3-4 hours;
   c) optionally isolating crystalline Fexofenadine characterized by the following X-ray powder diffraction pattern (d values in Å): 23.11, 11.50, 8.29, 7.03, 6.67, 6.16, 6.02, 5.75, 5.43, 5.33, 5.07, 4.69, 4.63, 4.44, 4.20, 4.15, 4.07, 3.55, and 3.44 obtained in step b) by conventional methods accompanied by drying at below 100° C.;
   d) suspending the isolated crystalline Fexofenadine obtained in step c) or adding to the reaction mixture of step b), a mixture of a nonpolar organic solvent or an organic solvent and isopropanol;
   e) adjusting the pH of the solution of step d) to 1 to 3 with a solvent containing hydrogen chloride;
   f) filtering the solution obtained in step e) to remove particulate matter;
   g) seeding the solution of step f) with several crystals of crystalline fexofenadine hydrochloride according to claim 6 and stirring the reaction mass at ambient temperature to separate a solid;
   h) filtering the solid obtained in step g) followed by washing with a nonpolar organic solvent, organic solvent or hydrocarbon solvent; and
   i) drying the crystalline Fexofenadine hydrochloride.
5. The process as claimed in claim 2 step (d), wherein the solvent containing hydrogen chloride is selected from methanol, ethanol, isopropanol or t-butanol.
6. The process as claimed in claim 4 wherein the hydrocarbon solvent is selected from hexane or cyclohexane.
7. The process as claimed in claim 2, wherein the non polar solvent is selected from toluene or xylene.
8. The process as claimed in claim 3, wherein the non polar solvent is selected from toluene or xylene.
9. The process as claimed in claim 4, wherein the non polar solvent is selected from toluene or xylene.
10. The process as claimed in claim 2, wherein the ($C_1$-$C_3$) alkanol is methanol, ethanol or propanol.
11. The process as claimed in claim 3, wherein the ($C_1$-$C_3$) alkanol is methanol, ethanol or propanol.
12. The process as claimed in claim 4, wherein the ($C_1$-$C_3$) alkanol is methanol, ethanol or propanol.
13. The process as claimed in claim 2, wherein the nonpolar organic solvent is n-hexane, hexane, octane, nonane or cyclohexane.
14. The process as claimed in claim 3, wherein the nonpolar organic solvent is n-hexane, hexane, octane, nonane or cyclohexane.
15. The process as claimed in claim 4, wherein the nonpolar organic solvent is n-hexane, hexane, octane, nonane or cyclohexane.
16. The process as claimed in claim 2, wherein the organic solvent is selected from ($C_1$-$C_4$) alkyl acetate.
17. The process as claimed in claim 3, wherein the organic solvent is selected from ($C_1$-$C_4$) alkyl acetate.
18. The process as claimed in claim 4, wherein the organic solvent is selected from ($C_1$-$C_4$) alkyl acetate.
19. The process as claimed in claim 2, wherein the organic solvent is ethyl acetate.
20. The process as claimed in claim 3, wherein the organic solvent is ethyl acetate.
21. The process as claimed in claim 4, wherein the organic solvent is ethyl acetate.
22. The process as claimed in claim 3 step (f), wherein the solvent containing hydrogen chloride is selected from methanol, ethanol, isopropanol or t-butanol.
23. The process as claimed in claim 4 step (e), wherein the solvent containing hydrogen chloride is selected from methanol, ethanol, isopropanol or t-butanol.
24. A compound, which is crystalline form X of Fexofenadine Hydrochloride.

* * * * *